(12) United States Patent
Geiger

(10) Patent No.: US 7,048,721 B2
(45) Date of Patent: May 23, 2006

(54) NEEDLELESS SYRINGE

(75) Inventor: Andreas Geiger, Kirchlengern (DE)

(73) Assignee: Buender Glas GmbH, Buende (DE)

( * ) Notice: Subject to any disclaimer, the term of this patent is extended or adjusted under 35 U.S.C. 154(b) by 16 days.

(21) Appl. No.: 10/397,144

(22) Filed: Mar. 26, 2003

(65) Prior Publication Data

US 2004/0193105 A1   Sep. 30, 2004

(51) Int. Cl.
*A61M 5/00* (2006.01)

(52) U.S. Cl. ..................... 604/232; 604/122

(58) Field of Classification Search ............ 604/68–73, 604/90, 131, 156, 181–184, 187, 207–210, 604/220–221, 218, 224, 228, 232, 246, 82, 604/122, 129
See application file for complete search history.

(56) References Cited

U.S. PATENT DOCUMENTS

| | | | |
|---|---|---|---|
| 3,527,212 A | | 9/1970 | Wesley |
| 4,036,225 A | * | 7/1977 | Maury .................... 604/88 |
| 4,529,403 A | | 7/1985 | Kamstra |
| 4,553,962 A | * | 11/1985 | Brunet .................... 604/198 |
| 5,531,255 A | * | 7/1996 | Vacca ..................... 141/285 |
| 5,630,800 A | * | 5/1997 | Blank et al. ............... 604/82 |
| 5,704,918 A | | 1/1998 | Higashikawa |
| 6,149,628 A | * | 11/2000 | Szapiro et al. ............ 604/191 |
| 6,740,062 B1 | * | 5/2004 | Hjertman ................. 604/187 |
| 2002/0035348 A1 | * | 3/2002 | Hjertman ................. 604/272 |

FOREIGN PATENT DOCUMENTS

| | | |
|---|---|---|
| DE | 2 258 372 | 6/1973 |
| EP | 0 896 827 A1 | 2/1999 |
| EP | 1 013 299 A1 | 6/2000 |
| GB | 1 416 303 | 12/1975 |

* cited by examiner

*Primary Examiner*—LoAn H. Thanh
(74) *Attorney, Agent, or Firm*—Laurence A. Greenberg; Werner H. Stemer; Ralph E. Locher

(57) ABSTRACT

A needleless syringe that provides the necessary high pressure, is easily generated despite the utilization of relatively thin-walled glass ampules for storing an injectable medicine. A plastic body of the needleless syringe contains an interior space surrounded by walls. The interior space is divided into a first region with one end open to the outside and an adjoining second region. A glass ampule containing a medicine, which is sealed at both ends with plunger-type stoppers, is disposed in the first region. The second region contains an output opening leading through the wall of the plastic body. A ram is provided with which the stopper that is averted from the second region can be pushed into the glass ampule and into the second region.

11 Claims, 1 Drawing Sheet

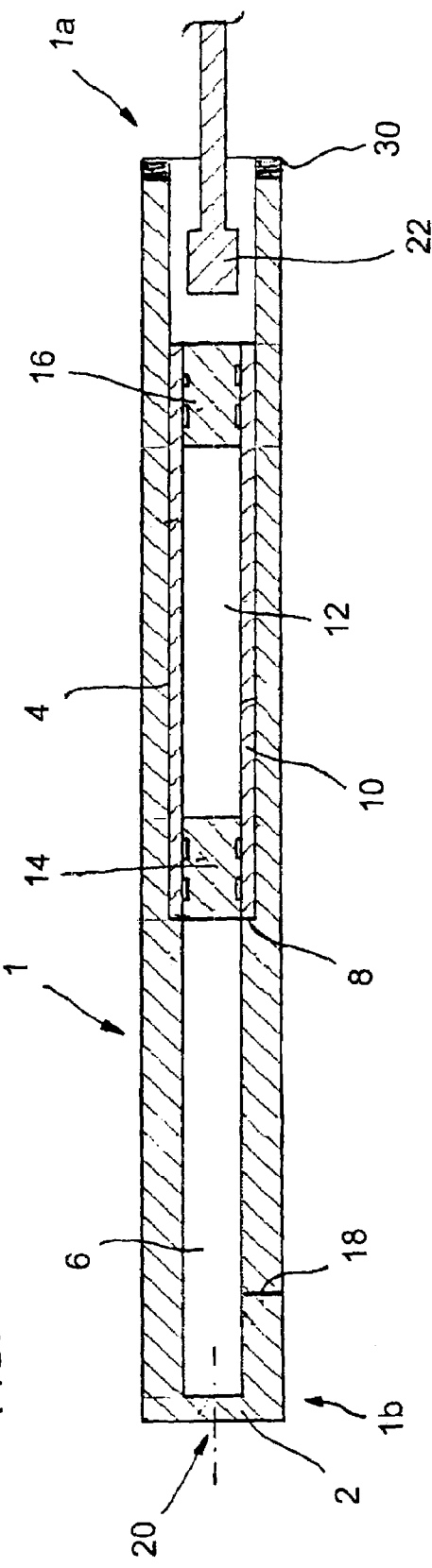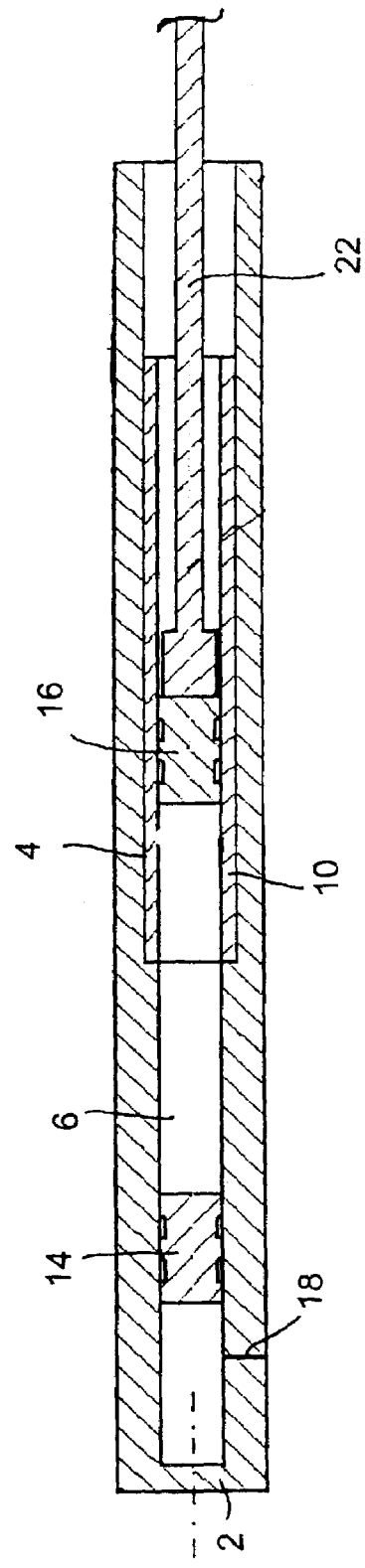

NEEDLELESS SYRINGE

BACKGROUND OF THE INVENTION

Field of the Invention

The invention relates to needleless syringes for injecting medication under the skin of a patient under high pressure.

The advantage of needleless syringes is that they are more easily accepted by sensitive patients than syringes with needles. Furthermore, neither medical personnel nor patients can become infected by contact with a needle of a used syringe.

U.S. Pat. No. 3,527,212 describes a needleless syringe with an outer plastic body in whose cylindrical interior there is a displaceable ampule under high pressure, which contains a medicine. The ampule has an opening that is sealed with a destructible membrane and with which the ampule can be moved towards a stationary needle, whereby the needle is connected to an output opening of the syringe that leads outside. Given corresponding displacement of the ampule, the needle punctures the membrane, and the medication is pushed out through the output opening under high pressure.

The disadvantage of that prior art is that, for medical reasons (contamination), the ampule should consist of glass; however, because glass cannot tolerate high internal pressure, the ampule must be constructed either with very thick walls or from a different material. Furthermore, an additive is needed for pressure generation, for instance $CO_2$, and a membrane must be provided.

SUMMARY OF THE INVENTION

It is accordingly an object of the invention to provide a needleless syringe that overcomes the above-mentioned disadvantages of the prior art devices of this general type, in which relatively thin-walled glass ampules can be utilized for storing the injection medication, and the necessary high pressure can nevertheless be easily generated.

With the foregoing and other objects in view there is provided, in accordance with the invention, a needleless syringe. The syringe contains a plastic body having walls defining an interior space surrounded by the walls. The interior space has a first region with one end open to an outside, and a second region adjacent to the first region. One of the walls has an output opening formed therein in the second region leading to the outside. A glass ampule contains a medicine disposed in the first region and has ends. Plunger-type stoppers, including a first stopper and a second stopper, are disposed at and seal both of the ends of the glass ampule. The first stopper is distal from the second region of the plastic body. A ram is attached to the plastic body, the ram pushes the first stopper along the glass ampule and into the second region.

It is expediently provided that the plastic body is constructed with thicker walls around the second region than the first region.

The plastic body advantageously has a cylindrical exterior and a cylindrical interior, whereby the inner diameter of the first region is greater than that of the second region. The second region can be provided with a boundary wall containing a ventilation opening.

It can be provided that the distance between the boundary wall and the output opening corresponds to the length of the stopper adjacent the second region.

It is expediently provided that the inner diameter of the glass ampule corresponds to the inner diameter of the second region. It can be further provided that the length of the second region substantially matches the length of the liquid column contained in the glass ampule, not including the length of the stopper adjoining the second region.

In a development of the invention, it can be provided that, in the region of the first region, the plastic body is provided with an external thread onto which an actuating device that acts on the ram is or can be screwed.

Other features which are considered as characteristic for the invention are set forth in the appended claims.

Although the invention is illustrated and described herein as embodied in a needleless syringe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic, cross-sectional view of a needleless syringe in an initial condition according to the invention; and FIG. 2 is a cross-sectional view of the syringe according to FIG. 1 in a partly activated state.

DESCRIPTION OF THE PREFERRED EMBODIMENTS

Referring now to the figures of the drawing in detail and first, particularly, to FIG. 1 thereof, there is shown a cross-sectional view of a needleless syringe with an externally and internally cylindrical plastic body 1 with an open end 1a and an end 1b which is sealed by a radial boundary wall 2. An interior space of the plastic body 1 is subdivided into a first region 4 and a second region 6. An inner diameter of the first region 4 being greater than that of the second region 6. At a transition between the two regions 4 and 6 there is a shoulder 8.

A hollow-cylindrical glass ampule 10 is inserted into the first region 4 until it contacts the shoulder 8. The glass ampule 10 contains a medicine 12 in its interior and is sealed at both ends by plunger-type stoppers 14, 16.

At a distance from the first section 4, the plastic body 1 contains a lateral output opening 18 that serves for delivering medicine 12, and a ventilation opening 20 in the region of its boundary wall 2, which is represented only by indication.

A ram 22 serves for pushing the stopper 16 that is averted from the second region 6, which is located in the vicinity of the open end 1a of the plastic body 1, whereby it can be provided that the ram 22 is actuated by a suitable actuating device which can be screwed onto an external thread 30 of the plastic body 1, for example.

The wall thickness of the glass ampule 10 corresponds to the radius difference between the first and second regions; that is, the inner diameter of the glass ampule 10 is substantially identical to the inner diameter of the first region 4 of the interior space of the plastic body 1, so that medicine can be delivered as described below.

As represented in FIG. 2, first the stopper 16 adjoining the open end 1a is pushed without substantial force into the glass ampule with the aid of the ram 22, whereby the second stopper 14 is forced into the second region 6 of the interior space of the plastic body 1 by virtue of the incompressibility of the liquid medicine. This process continues until the stopper 14 contacts the boundary wall 2, whereby trapped air can escape through the ventilation opening 20. As emerges from the drawing, the output opening 18 is disposed at a distance from the boundary wall 2 such that it is no longer covered by the stopper 14 when the stopper is in contact with the boundary wall 2.

When the ram 22 is moved rapidly forward after achieving the described intermediate position, a substantial pressure can be generated inside the first region 4, so that the medicine 12 is ejected through the output opening 18 under high pressure. This process continues until the second stopper 16 makes contact with the first stopper 14, and the entire amount of the medicine 12 has been ejected.

The advantage of the inventive embodiment is that the relatively pressure-sensitive glass ampule 10 is only subjected to an insignificant internal pressure during the first movement phase, whereas the high internal pressure generated in the injection phase acts exclusively inside the second region 6, which is surrounded by the strong outer walls. This is also achieved by the substantial correspondence between the length of the second region and the length of a liquid column contained in the glass ampule 10 (excluding the length of the stopper adjoining the second region).

The plastic body 1 can be reusable, so that another glass ampule 10 can be utilized, for which the plastic body 1 need simply be sterilized.

Alternatively, the needleless syringe can conceivably be non-reusable.

I claim:

1. A needleless syringe, comprising:
   a plastic body having walls defining an interior space surrounded by said walls, said interior space having an inner surface, a first region with one end open to an outside, and a second region adjacent to said first region, one of said walls having an output opening formed therein in said second region leading to the outside;
   a glass ampule containing a medicine disposed in said first region and having ends;
   plunger-type stoppers, including a first stopper and a second stopper, disposed at and sealing both of said ends of said glass ampule, said second stopper being distal from said first stopper in said plastic body;
   a ram positioned within said plastic body, said ram pushing said first stopper along said glass ampule and into said second region;
   said first and second stoppers being surrounded by said inner surface along an entire traverse path of said first and second stoppers;
   said first stopper having a first periphery and said second stopper having a second periphery and said first and second peripheries abutting said inner surface along said entire traverse path of said first and second stoppers; and
   said inner surface of said second region having a ventilation opening formed therein, thereby, upon injection, content of said second region escaping through said ventilation opening and only content of said glass ampule being injected though said output opening.

2. The syringe according to claim 1, wherein said walls of said plastic body are thicker in said second region than in said first region.

3. The syringe according to claim 1, wherein said plastic body has a shape that is externally and internally cylindrical, said first region having a larger inner diameter than said second region.

4. The syringe according to claim 1, wherein said second region has a boundary wall and said ventilation opening is formed in said boundary wall.

5. The syringe according to claim 4, wherein a distance between said boundary wall and said output opening corresponds to a length of said second stopper adjacent to said second region.

6. The syringe according to claim 1, wherein said glass ampule has an inner diameter corresponding to an inner diameter of said second region.

7. The syringe according to claim 6, wherein:
   said medicine in said glass ampule forms a liquid column;
   said second region has a length substantially corresponding to a length of said liquid column contained in said glass ampule, excluding a length of said second stopper adjacent to said second region.

8. A needleless syringe, comprising:
   a plastic body having walls defining an interior space surrounded by said walls, said interior space having an inner surface, a first region with one end open to an outside, and a second region adjacent said first region, one of said walls having an output opening formed therein in said second region leading to the outside;
   a glass ampule containing a medicine disposed in said first region and having ends;
   plunger-type stoppers, including a first stopper and a second stopper, disposed at and sealing both of said ends of said glass ampule, said second stopper being distal from said first stopper in said plastic body;
   a ram positioned within said plastic body, said ram pushing said first stopper along said glass ampule and into said second region;
   said first and second stoppers being surrounded by said inner surface along an entire traverse path of said first and second stoppers;
   said first stopper having a first periphery and said second stopper having a second periphery and said first and second peripheries abutting said inner surface along said entire traverse path of said first and second stoppers; and
   said walls of said plastic body being thicker in said second region than in said first region.

9. A needleless syringe, comprising:
   a plastic body having walls defining an interior space surrounded by said walls, said interior space having an inner surface, a first region with one end open to an outside, and a second region adjacent said first region, one of said walls having an output opening formed therein in said second region leading to the outside;
   a glass ampule containing a medicine disposed in said first region and having ends;
   plunger-type stoppers, including a first stopper and a second stopper, disposed at and sealing both of said ends of said glass ampule, said second stopper being distal from said first stopper in said plastic body;
   a ram positioned within said plastic body, said ram pushing said first stopper along said glass ampule and into said second region;

said first and second stoppers being surrounded by said inner surface along an entire traverse path of said first and second stoppers;

said first stopper having a first periphery and said second stopper having a second periphery and said first and second peripheries abutting said inner surface along said entire traverse path of said first and second stoppers; and said plastic body having a shape being externally and internally cylindrical, said first region having a larger inner diameter than said second region.

10. A needleless syringe, comprising:

a plastic body having walls defining an interior space surrounded by said walls, said interior space having an inner surface, a first region with one end open to an outside, and a second region adjacent said first region, one of said walls having an output opening formed therein in said second region leading to the outside;

a glass ampule containing a medicine disposed in said first region and having ends;

plunger-type stoppers, including a first stopper and a second stopper, disposed at and sealing both of said ends of said glass ampule, said second stopper being distal from said first stopper in said plastic body;

a ram positioned within said plastic body, said ram pushing said first stopper along said glass ampule and into said second region;

said first and second stoppers being surrounded by said inner surface along an entire traverse path of said first and second stoppers;

said first stopper having a first periphery and said second stopper having a second periphery and said first and second peripheries abutting said inner surface along said entire traverse path of said first and second stoppers; and said glass ampule having an inner diameter corresponding to an inner diameter of said second region.

11. The syringe according to claim 10, wherein:

said medicine in said glass ampule forms a liquid column; and said second region has a length substantially corresponding to a length of said liquid column contained in said glass ampule, excluding a length of said second stopper adjacent said second region.

* * * * *